United States Patent
Pennick et al.

(10) Patent No.: US 10,850,136 B2
(45) Date of Patent: Dec. 1, 2020

(54) MOISTURISER BLEND

(75) Inventors: Graham Timothy Pennick, Selby (GB); Michael Andrew Oakley, Kingston Upon Hull (GB); Bhaven Chavan, Bradford (GB)

(73) Assignee: Croda International Plc

( * ) Notice: Subject to any disclaimer, the term of this patent is extended or adjusted under 35 U.S.C. 154(b) by 407 days.

(21) Appl. No.: 13/983,421

(22) PCT Filed: Jan. 24, 2012

(86) PCT No.: PCT/GB2012/050146
§ 371 (c)(1),
(2), (4) Date: Aug. 20, 2013

(87) PCT Pub. No.: WO2012/104604
PCT Pub. Date: Aug. 9, 2012

(65) Prior Publication Data
US 2013/0324499 A1 Dec. 5, 2013

(30) Foreign Application Priority Data
Feb. 5, 2011 (GB) .................................. 1101990.8

(51) Int. Cl.
| | | |
|---|---|---|
| *A61P 29/00* | (2006.01) | |
| *A61Q 19/00* | (2006.01) | |
| *A61K 8/34* | (2006.01) | |
| *A61K 8/36* | (2006.01) | |
| *A61K 8/37* | (2006.01) | |
| *A61K 8/02* | (2006.01) | |
| *A61K 8/06* | (2006.01) | |
| *A61K 8/55* | (2006.01) | |

(52) U.S. Cl.
CPC ............ *A61Q 19/00* (2013.01); *A61K 8/0216* (2013.01); *A61K 8/062* (2013.01); *A61K 8/342* (2013.01); *A61K 8/361* (2013.01); *A61K 8/37* (2013.01); *A61K 8/55* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 5,603,940 A | 2/1997 | Candau et al. | |
| 5,658,575 A | 8/1997 | Ribier et al. | |
| 5,662,894 A | 9/1997 | McManus | |
| 6,066,328 A | 5/2000 | Ribier et al. | |
| 6,927,240 B2 | 8/2005 | Schmid et al. | |
| 2003/0147963 A1* | 8/2003 | De Moragas | A61K 8/02 424/488 |
| 2008/0200544 A1 | 8/2008 | Takeda et al. | |
| 2008/0292668 A1 | 11/2008 | Baars et al. | |
| 2010/0173027 A1 | 7/2010 | Kroepke et al. | |
| 2010/0190740 A1 | 7/2010 | L'Alloret et al. | |
| 2010/0284948 A1 | 11/2010 | Ohrmann | |

FOREIGN PATENT DOCUMENTS

| | | | |
|---|---|---|---|
| EP | 0641557 A1 | 3/1995 | |
| JP | 08127526 | 5/1996 | |
| JP | 09175935 | 7/1997 | |
| JP | 09512277 | 12/1997 | |
| JP | 2010505886 | 2/2010 | |
| JP | 2010143903 | 7/2010 | |
| KR | 2003-0085903 | 11/2003 | |
| WO | 9528913 | 11/1995 | |
| WO | WO 95/28913 | 11/1995 | |
| WO | WO 2007147904 A2 * | 12/2007 | A61K 8/062 |

OTHER PUBLICATIONS

Lubrizol (Schercemol™ 1818 Ester . Technical Data Sheet Lubrizol Advanced Materials, Inc. / 9911 Brecksville Road, Cleveland, Ohio TDS-376 Edition: Jan. 14, 2009.*
Friberg, Stig E.; "Micelles, Microemulsions, Liquid Crystals, and the Structure of Stratum Corneum Lipids"; J. Soc. Cosmet. Chem., 1990, 41, 155-171.
The EPO, International Search Report of PCT/GB2012/050146, dated Oct. 14, 2013.
Notice of Reasons for Rejection for Application No. 2013-552258 dated Aug. 4, 2015.
Notice of Reasons for Rejection for Japanese Appiication No. 2013-552258, dated Jul. 12, 2016, 4 pages.
Second Korean Notice of Preliminary Rejection (English Translation) for Korean Application No. 10-2013-7023451, dated Nov. 14, 2018—8 pages.
Decision to Grant for Russian Application No. 2013140833/15, dated Nov. 15, 2017, 5 pages.
Russian Office Action for Russian Application No. 2013140833/15, dated Oct. 28, 2015, including English language translation, 8 pages.

* cited by examiner

*Primary Examiner* — Layla Soroush
(74) *Attorney, Agent, or Firm* — RatnerPrestia

(57) ABSTRACT

A blend for use in a personal care composition comprises a dialkyl amphiphilic component and an ester of a long chain branched fatty acid and a long chain branched alcohol. The blend can be pastillated and/or flaked, and can be used as the oil phase of an oil-in-water emulsion. The blend can be used in a moisturiser composition for moisturising skin.

14 Claims, 2 Drawing Sheets

MOISTURISER BLEND

CROSS-REFERENCE TO RELATED APPLICATIONS

This application is the U.S. National Phase application of PCT International Application No. PCT/GB2012/050146, filed Jan. 24, 2012, and claims priority of British Patent Application No. 1101990.8, filed Feb. 5, 2011, the disclosures of both of which are incorporated herein by reference in their entireties for all purposes.

FIELD OF THE INVENTION

The present invention relates to a composition or blend for use in a personal care application. In particular, the invention relates to a composition or blend of components providing an improved moisturisation effect and moisture retention effect.

The invention also relates to a personal care composition which provides superior effects with regard to moisturisation and moisture retention, particularly the moisturisation and moisture retention of human skin.

BACKGROUND OF THE INVENTION

Human skin is composed of several morphologically different layers. The outer layer of the skin, the epidermis, is composed of 4 to 5 sub-layers depending on the region of the skin being considered. These sub-layers are, in descending order from the outer surface of the skin, the stratum corneum, the stratum lucidum (present only in thick skin, for example soles of feet and palms of hands), the stratum granulosum, the stratum spinosum and the stratum basale.

The term "viable epidermis" is used to refer to the four underlying layers of the epidermis, and is a dynamic, constantly self-renewing tissue that generates the stratum corneum. Skin cells, known as kertinocytes are synthesised by the basal layer, and start to differentiate as they migrate upwards through the stratum spinosum and stratum granulosum undergoing a number of changes in both structure and composition. The final step in keratinocyte differentiation is the formation of the stratum corneum and transformation into corneocytes.

Corneocytes are flat dead cells filled with keratin filaments and water, which are surrounded by a densely cross linked protein layer that is in turn chemically linked to a lipid envelope. The lipid envelope acts as an interface between the corneocytes, which are hydrophilic, and the lipids, that are lipophilic and non-polar, that surround the corneocytes. This lipid matrix consists of ceramides, cholesterol and free fatty acids in an approximately equal ratio. These intercellular lipids are excreted from the characteristic organelles (lamellar bodies) at the stratum granulosum/corneum interface during keratinocyte differentiation.

The stratum corneum is primarily responsible for the water permeability barrier function of the skin. Hence it can prevent the skin being in a dry skin state. The stratum corneum uses three main mechanisms to provide such a water permeability barrier. Firstly, the intercellular lipids which form the only continuous pathway through the stratum corneum. Secondly, the corneocytes themselves with associated hydrophobic envelopes linked by corneodesmosomes. Finally, the presence of intracellular and extracellular hygroscopic materials called natural moisturising factors all contribute to the water permeability barrier.

It has been reported that the intercellular lipids in human skin form two lamellar phases parallel to the skin surface with repeat distances of approximately 6 and 13 nm, referred to as the short periodicity phase and the long periodicity phase. Within these lamellar phases the lipids are highly organised in a tightly-packed, mostly lateral, orthorhombic state. The orthorhombic packing, in addition to the presence of the long periodicity phase, is thought to be critical for normal barrier functionality.

It has also been reported in the scientific literature that the presence of long chain fatty acids in the lipid matrix is needed to induce the formation of the orthorhombic lattice in ceramide and cholesterol mixtures. Furthermore, it has been shown, using tape stripping and electron microscopy, that this highly organised lipid lamellar phase is missing from between the corneocytes in the outer most dry skin layers.

Key to the underlying cause behind the condition commonly called 'dry skin' or cosmetic xerosis is a perturbation of the water gradient within the stratum corneum. Therefore, there exists a need to provide a formulation that can replenish the water gradient in the stratum corneum in dry skin, for example for persons with dry skin conditions.

It is an object of the present invention to address these and other disadvantages associated with the prior art.

SUMMARY OF THE INVENTION

According to a first aspect of the present invention, there is provided a blend comprising:
 a) at least one dialkyl amphiphilic component; and
 b) at least one, ester of a long chain branched fatty acid and a long chain branched alcohol According to a second aspect of the present invention, there is provided a blend for use in a personal care composition, the blend consisting essentially of:
 a) a dialkyl amphiphilic component;
 b) an ester of a long chain branched fatty acid and a long chain branched alcohol;
 c) a long chain fatty acid; and
 d) a long chain alcohol.

According to a third aspect of the present invention, there is provided the use of a blend according to the first or second aspect of the present invention in a moisturising formulation for moisturising skin.

According to a fourth aspect of the present invention, there is provided a blend according to the first or second aspect of the present invention for topical application to the skin or mucosa having an improved water vapour transmission rate.

According to a fifth aspect of the present invention, there is provided a pastillated and/or flaked product comprising a blend according to either the first or the second aspect of the present invention.

According to a sixth aspect of the present invention, there is provided an oil-in-water emulsion, wherein the oil phase comprises a blend according to either the first or the second aspect of the present invention.

BRIEF DESCRIPTION OF THE DRAWINGS

The invention is further illustrated by reference to the accompanying drawings in which.

DETAILED DESCRIPTION OF THE INVENTION

Figure 1:
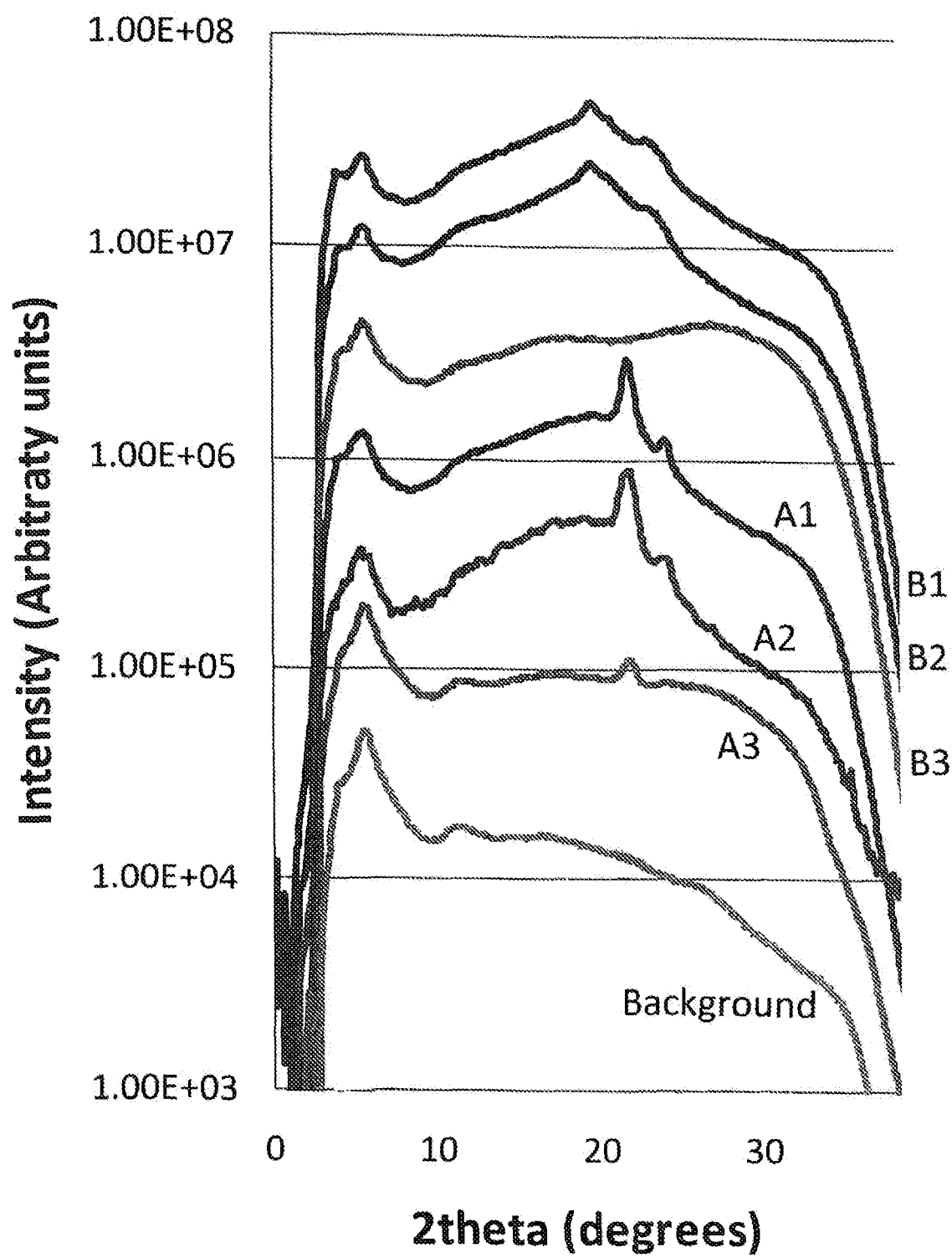
FIG. 1 shows wide angle x-ray scattering patterns for comparative emulsions and test emulsions.

According to a first aspect of the present invention, there is provided a blend comprising:
a) at least one dialkyl amphiphilic component; and
b) at least one, ester of a long chain branched fatty acid and a long chain branched alcohol Preferably, blend is suitable for use as the oil component of an oil-in-water emulsion. Preferably, the blend is suitable for use in a personal care composition, preferably a moisturiser composition.

By the term "long chain" in the present specification, it is meant a carbon backbone chain of between 12 and 30 carbon atoms, preferably between 16 and 26, more preferably between 16 and 22 carbon atoms.

By the term "dialkyl amphiphilic component" as used herein, it is meant a component having both hydrophilic and lipophilic properties. The dialkyl amphiphilic component comprises a large head group, which is preferably hydrophilic, and a long tail group comprising two alkyl groups, preferably long chain alkyl groups, which is preferably hydrophobic. The dialkyl amphiphilic component is preferably capable of forming lipid bilayers in an aqueous medium.

The dialkyl amphiphilic component can be ionic, i.e. anionic or cationic, or non-ionic. The dialkyl amphiphilic component may be alkoxylated, preferably ethoxylated.

When the dialkyl amphiphilic component is anionic, the anionic functionality can be provided by, for example, a phosphorus acid group or salt thereof or a sulphur acid group or salt thereof. Suitable phosphorus acid groups include —OP(=O)(OH)O—, —(OA)$_n$OP(=O)(OH)O—, and —(OA)$_n$OP(=O)(OH)O(AO)$_m$—, where A represents an alkylene group, for example ethylene, propylene, and so on, and m and n are from 1 to 60, desirably 5 to 30. Suitable sulphur acid groups include sulphosuccinate: —OC(O)CH(SO$_3$H)CH$_2$C(O)O—, and alkoxylated sulphosuccinates: —(OA)$_n$OC(O)CH(SO$_3$H)CH$_2$C(O)O—, and —(OA)$_n$OC(O)CH(SO$_3$H)CH$_2$C(O)O(AO)$_m$—, where A, n and m are as defined above.

When the dialkyl amphiphilic component is cationic, the cationic functionality may be provided by, for example, dialkyl dimethyl amines: —N$^+$(CH$_3$)$_2$—, or imidazolines.

When the dialkyl amphiphilic component is nonionic, the nonionic hydrophilic functionality may be provided by, for example, esters of sorbitol, sorbitan, sucrose and polyglycerol, and alkoxylates thereof.

Preferably, the dialkyl amphiphilic component is ionic, more preferably anionic. Preferably, the anionic functionality is provided by a phosphorus acid group or a salt thereof. More preferably, the anionic functionality is provided by a phosphate group.

Preferably, the dialkyl amphiphilic component is present in the blend in the form of a salt. Preferably, the salt forming moiety is an alkali metal, particularly Li, Na or K, ammonium, including amine or hydroxyl-substituted amine, e.g. alkanoamine, onium, or amine, particularly alkylamine, especially tertiary alkylamine and hydroxy-substituted amine, e.g. alkanoamine, especially tertiary alkanoamine such as triethanolamine. Salts can generally be made from free acid precursors by direct reaction with an appropriate base. Desirably, the salt forming moiety is an alkali metal, preferably Na or K, most preferably K.

The dialkyl functionality of the amphiphilic component may be provided by any two suitable alkyl groups. Preferably, the alkyl groups are long chain alkyl groups. The alkyl groups may the same or different. Each alkyl group may be independently selected from the group including linear and branched alkyl groups. By the term alkyl, it is meant any saturated hydrocarbyl group which is a monovalent radical having the general formula $C_nH_{2n+1}$. The alkyl groups may each independently contain one or more unsaturated bonds, i.e. one or more double C=C bonds. Preferably, each alkyl group is independently selected from the group comprising C10 to C30 alkyl groups, more preferably, C12 to C26 alkyl groups, desirably C14 to C22 alkyl groups. Preferably, the alkyl groups are the same as each other. Desirably, the alkyl groups are C16 alkyl groups.

The dialkyl amphiphilic component may be present in combination with a monoalkyl amphiphilic component. When present, the monoalkyl amphiphilic component is a monoalkyl equivalent of the dialkyl amphiphilic component, i.e. the monoalkyl amphiphilic component is the same as the dialkyl amphiphilic component with one alkyl group substituted by H or a short chain alkyl group, for example a methyl, ethyl or propyl group.

Preferably, the dialkyl amphiphilic component has a packing parameter, R, of between approximately 0.25 and 1.25, more preferably between approximately 0.3 and 1.1, desirably between approximately 0.5 and 1. The packing parameter, R, of the dialkyl amphiphilic component preferably corresponds to a cylindrical or lamellar amphiphilic association structure. The packing parameter is calculated according to the formula:

$$R = v/al,$$

in which v is the real volume of the dialkyl chain, a is the cross-sectional area of the amphiphilic component head group, i.e. the ionic or non-ionic group, and l is the approximate length of the amphiphilic component hydrocarbon chain. The packing parameter is described in more detail in S. Friberg, J. Soc. Cosmet. Chem., 1990, 41, 155-171, the contents of which is hereby incorporated by reference.

Preferably, the dialkyl amphiphilic component is present in the blend at a concentration of between approximately 1 to 75% by weight of the total blend, preferably approximately 5 to 50% by weight, more preferably approximately 10 to 35% by weight, most preferably approximately 15 to 25% by weight.

Preferably, the ester of a long chain branched fatty acid and a long chain branched alcohol comprises a mixture of compounds having mono- and poly-branching in the acid and alcohol originating parts of the compound. Preferably, the long chain fatty acid and long chain fatty alcohol are alkyl branched.

Fatty acids suitable for use herein can be obtained from natural sources such as, for example plant or animal esters. For example, the acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures employed. Resin acids, such as those present in tall oil, may also be used.

The long chain fatty acid component of the ester may comprise a mixture of branched and linear long chain fatty acids. Preferably, the fatty acid mixture comprises greater than 70%, more preferably in the range from 73 to 95%, particularly 77 to 90%, and especially 80 to 85% by weight of branched fatty acids, and less than 30%, more preferably in the range from 5 to 27%, particularly 10 to 23%, and especially 15 to 20% by weight of linear fatty acids, both based on the total weight of fatty acids present.

The long chain branched fatty acid component of the ester preferably comprises alkyl side branches (attached directly to a carbon atom of the longest linear chain) having on average less than 3, more preferably less than 2.5, particularly in the range from 1.05 to 2, and especially 1.1 to 1.4 carbon atoms, i.e. the side branches are predominantly methyl groups. In a preferred embodiment of the invention, greater than 50%, more preferably greater than 60%, particularly in the range from 70 to 97%, and especially 80 to 93% by number of the side-branched groups are methyl groups. In a further preferred embodiment, greater than 30%, more preferably greater than 40%, particularly in the range from 45 to 90%, and especially 50 to 80% by number of the branched fatty acids contain single methyl side branches.

Suitable branched chain fatty acids for use in the present invention include iso-acids such as isostearic acid, isopalmitic acid, isomyristic acid, isoarachidic acid and isobehenic acid; neo-acids such as neodecanioc acid; and/or anti-iso acids. Preferably, the branched chain fatty acid is an iso-acid. Isostearic acid is preferred.

The long chain branched fatty alcohol component of the ester is preferably a C12 to C30 alcohol, preferably a C14 to C26 alcohol and most preferably a C16 to C22 and especially C18 fatty alcohol.

Preferably, the long chain branched fatty alcohol component of the ester is made from the long chain fatty acid component of the ester. Therefore, preferably, the same preferences apply to the long chain branched fatty alcohol component of the ester as to the long chain branched fatty acid component of the ester. Preferably, the chain length of the long chain fatty alcohol component of the ester is the same as the chain length of the long chain fatty acid component of the ester.

Alternatively, a mixture of branched and linear long chain fatty alcohols may be present in the fatty alcohol component of the ester. Preferably, the alcohol mixture comprises greater than 70%, more preferably in the range from 73 to 95%, particularly 77 to 90%, and especially 80 to 85% by weight of branched alcohols, and less than 30%, more preferably in the range from 5 to 27%, particularly 10 to 23%, and especially 15 to 20% by weight of linear alcohols, both based on the total weight of long chain alcohol present.

Suitable branched long chain alcohols include iso-alcohols such as isostearyl alcohol, isotetradecanol, isocetyl alcohol, isoarachidyl alcohol, isobehenyl alcohol and isolignoceryl alcohol; neo-alcohols such as neocapric alcohol; and/or anti-iso alcohols. Preferably, the branched chain fatty alcohol is an iso-alcohol. Isostearyl alcohol is preferred.

Preferably, the ester is an ester of a C16-22 branched fatty acid and a C16-22 branched alcohol. The fatty acid and alcohol may comprise the same number of carbon atoms, or a different number of carbon atoms. Preferably, the fatty acid and alcohol comprise the same number of carbon atoms.

The ester may comprise one or more variations selected from the group comprising mono-branched acid and poly-branched alcohol, mono-branched acid and mono-branched alcohol, poly-branched acid and mono-branched alcohol, and poly-branched acid and poly-branched alcohol. The ester may be selected from this group by any suitable separation method. For example, the selected ester may be selected from a mixture of esters using a clathration method.

Preferably, the ester comprises a C18 mono- and/or poly-branched fatty acid and a C18 mono- and/or poly-branched alcohol. Preferably, the ester comprises isostearyl isostearate.

Preferably, the ester is present in the blend at a concentration of between approximately 1 to 75% by weight of the total blend, preferably approximately 5 to 50% by weight, more preferably approximately 14 to 35% by weight, most preferably approximately 18 to 27% by weight.

Preferably, the ester of a long chain branched fatty acid and a long chain branched alcohol and the dialkyl amphiphilic component are present in the blend at a ratio by weight of in the region of approximately 10:1 to approximately 1:10, preferably in the region of approximately 5:1 to approximately 1:5, more preferably in the region of approximately 2:1 to 1:2. Desirably, the ester of a long chain branched fatty acid and a long chain branched alcohol and the dialkyl amphiphilic component are present in the blend at a ratio by weight of in the region of approximately 1.25:1.

Additionally, a long chain fatty acid or a salt thereof may be present in the blend. When present, the long chain fatty acid is preferably a C12 to C32 chain acid, preferably C16 to C30, more preferably C18 to C28 and most preferably C18 to C24. The long chain fatty acid may be branched or linear. Preferably, the fatty acid is linear.

Long chain fatty acids suitable for use herein can be obtained from the same natural sources as the long chain fatty acid component of the ester.

A mixture of long chain fatty acids may be present in the blend. Preferably, when present, the fatty acid mixture comprises greater than 70%, more preferably in the range from 73 to 95%, particularly 77 to 90%, and especially 80 to 85% by weight of linear fatty acids, and less than 30%, more preferably in the range from 5 to 27%, particularly 10 to 23%, and especially 15 to 20% by weight of branched fatty acids, both based on the total weight of long chain fatty acids present.

Suitable long chain fatty acids for use in the present invention include lauric acid, myristic acid, palmitic acid, stearic acid, arachidic acid, behenic acid, lignoceric acid and cerotinic acid. Preferably, the or each long chain fatty acid is selected from the group comprising stearic acid, arachidic acid, behenic acid, lignoceric acid and cerotinic acid, more preferably from the group comprising arachidic acid, behenic acid and lignoceric acid. Most preferably, the long chain fatty acid is stearic acid or behenic acid.

Preferably, the long chain fatty acid or mixture thereof is present in the blend at a concentration of between approximately 1 to 75% by weight of the total blend, preferably approximately 5 to 50% by weight, more preferably approximately 14 to 35% by weight, most preferably approximately 18 to 25% by weight.

When a long chain fatty acid, or mixture of long chain fatty acids, is present in the blend, the acid, or mixture of acids, is present at a ratio by weight of in the region of approximately 10:1 to approximately 1:10, preferably in the region of approximately 5:1 to approximately 1:5, more preferably in the region of approximately 2:1 to 1:2 with the ester of a long chain branched fatty acid and a long chain branched alcohol. Desirably, the acid, or mixture of acids, and the ester of a long chain branched fatty acid and a long chain branched alcohol are present in the blend at a ratio by weight of in the region of approximately 1:1.

When a long chain fatty acid, or mixture of long chain fatty acids, is present in the blend, the acid, or mixture of acids, is present at a ratio by weight of in the region of approximately 10:1 to approximately 1:10, preferably in the region of approximately 5:1 to approximately 1:5, more preferably in the region of approximately 2:1 to 1:2 with the dialkyl amphiphilic component. Desirably, the acid, or mixture of acids, and the dialkyl amphiphilic component are present in the blend at a ratio by weight of in the region of approximately 1.25:1.

Additionally, a long chain alcohol may be present in the blend. When present, the long chain alcohol is preferably a C12 to C28 alcohol, preferably a C14 to C26 and most preferably a C16 to C24 alcohol. Preferably, the chain length of the alcohol is within 4 carbon atoms of, preferably within 2 carbon atoms of and desirably to the same as the alkyl chain length of the dialkyl amphiphilic component. The alcohol may be branched or linear. Preferably, the alcohol is linear.

Alternatively, a mixture of long chain alcohols may be present in the blend. In this case, preferably, the main component of the mixture of long chain alcohols is within 4 carbon atoms of, preferably within 2 carbon atoms of and desirably to the same as the alkyl chain length of the dialkyl amphiphilic component. Preferably, the alcohol mixture comprises greater than 70%, more preferably in the range from 73 to 95%, particularly 77 to 90%, and especially 80 to 85% by weight of linear alcohols, and less than 30%, more preferably in the range from 5 to 27%, particularly 10 to 23%, and especially 15 to 20% by weight of branched alcohols, both based on the total weight of long chain alcohol present.

Suitable long chain alcohols for use in the present invention include lauryl alcohol, tetradecanol, cetyl alcohol, stearyl alcohol, arachidyl alcohol, behenyl alcohol and lignoceryl alcohol. Preferably, the or each alcohol is selected from the group comprising lauryl alcohol, tetradecanol, cetyl alcohol, stearyl alcohol and arachidyl alcohol, more preferably from the group comprising tetradecanol, cetyl alcohol, stearyl alcohol. Most preferably, the long chain alcohol is cetyl alcohol.

Preferably, the long chain fatty alcohol or mixture thereof is present in the blend at a concentration of between approximately 10 to 85% by weight of the total composition, preferably approximately 15 to 70% by weight, more preferably approximately 25 to 55% by weight, most preferably approximately 30 to 40% by weight.

When a long chain alcohol, or mixture of long chain alcohols, is present in the blend, the alcohol, or mixture of alcohols, is present at a by weight ratio of in the region of approximately 12:1 to approximately 1:10, preferably in the region of approximately 6:1 to approximately 1:5, more preferably in the region of approximately 4:1 to 1:1 with the ester of a long chain branched fatty acid and a long chain branched alcohol. Desirably, the alcohol, or mixture of alcohols, and the ester of a long chain branched fatty acid and a long chain branched alcohol are present in the blend at a ratio by weight of in the region of approximately 1.6:1.

When a long chain alcohol, or mixture of long chain alcohols, is present in the blend, the alcohol, or mixture of alcohols, is present at a ratio by weight of in the region of approximately 10:1 to approximately 1:10, preferably in the region of approximately 5:1 to approximately 1:5, more preferably in the region of approximately 2:1 to 1:2 with the dialkyl amphiphilic component. Desirably, the alcohol, or mixture of alcohols, and the dialkyl amphiphilic component are present in the blend at a ratio by weight of in the region of approximately 2:1.

When a long chain alcohol, or mixture of long chain alcohols, and a long chain fatty acid, or mixture of long chain fatty acids, is present in the blend, the alcohol, or mixture of alcohols, is present at a ratio by weight of in the region of approximately 10:1 to approximately 1:12, preferably in the region of approximately 5:1 to approximately 1:6, more preferably in the region of approximately 2:1 to 1:4 with the long chain fatty acid, or mixture of long chain fatty acids. Desirably, the alcohol, or mixture of alcohols, and the long chain fatty acid, or mixture of long chain fatty acids are present in the blend at a ratio by weight of in the region of approximately 1:1.6. The long chain alcohol, or mixture of long chain alcohols, and the long chain fatty acid, or mixture of long chain fatty acids, it will be obvious to the skilled person that they may react to form an ester when both present in the blend. Preferably, the ester, when formed, is a cetyl behenate or cetyl stearate ester.

Preferably, the blend is anhydrous. By the term anhydrous, it is meant that the blend preferably comprises a maximum of 10% by weight water. More preferably, the blend comprises a maximum of 7% by weight water, most preferably, 5% and desirably 2% by weight. Preferably, the blend comprises 0.01% to 10% by weight water, preferably 0.05% to 5%, most preferably 0.1% to 2% by weight. The blend is neutralised with KOH, and then dried under vacuum to reduce the water content of the blend.

Preferably, the blend is pastillatable and/or flakable. Preferably, when present, the long chain fatty acid and/or long chain alcohol act as a pastillating or flaking agent. Preferably, the long chain fatty acid component of the blend is a pastillating and/or flaking agent.

The fluidity of the blend is important from a manufacturing standpoint, because without the proper final commercial handling properties, it will be extremely difficult to produce a commercially feasible product. During manufacture, a product has to be stirred, heated, cooled as needed, and often transferred in a fluid state to a flaking or pastillation line. All of this needs to be achieved at commercially viable temperatures, temperatures that will not degrade the product.

Flakes or pastilles are desired in the commercial industry because they are easily handled and incorporated into desired products. If the product is too gummy or pasty it will not be amendable to flaking or pastillation. Further, it will not often flow through the transfer line and will be difficult to heat or cool due to poor heat transfer.

In contrast, the claimed blends are free-flowing liquids above their melting points, making them easy to manufacture and easy to transfer and pump through transfer lines to flaking or pastillation equipment where it is chilled below its melting point and either broken up into easy to handle flakes or dispensed into pastilles and cooled. Thus, the claimed blends generally require the melting point to be below 100° C. in order to facilitate the transfer to the flaking or pastillation lines while maintaining the integrity of the blend. More preferably, the melting point of the blend is below 95° C., and most preferably below 90° C.

Whether a formulation is flakable is measured by pouring a relatively thin film (1/16"-1/8") of the heated composition onto a metal sheet and allowing it to cool. The cooled film is then "crumbled" or "scraped" into small flakes by any type of mechanical process. Thus, a successful formulation must possess two properties. First, the formulation must possess the property of being easily poured onto the sheet, thus forming a thin film. Second, once the formulation is allowed to cool, it must break up into flakes after crumbling or scraping. These flakes are consequently easily stored and re-melted as necessary.

Pastillation is a process in which small amounts of the desired formulation are dispensed into pastilles. These pastilles are then allowed to cool, forming a product, which is in solid form, but easily returned to a liquid state. Whether a formulation is capable of pastillation is measured by distributing small amounts of the heated formulation into pastilles. These pastilles are then allowed to cool. The pastilles must be easily melted without tremendous amounts of heat, preferably below the boiling point of water.

Preferably, the blend of the present invention is operable to be used in a personal care application, for example a personal care formulation. The composition of the present invention is preferably particularly advantageous for use in a moisturiser formulation.

When present in a personal care formulation, the blend is preferably present at a concentration of between 0.01% and 50% by weight of the total formulation, preferably between 0.05% and 20%, more preferably in the region of between 0.1% and 10%, and desirably between 1% and 4% by weight of the total formulation.

According to a second aspect of the present invention, there is provided a blend for use in a personal care composition, the blend consisting essentially of:
a) a dialkyl amphiphilic component;
b) an ester of a long chain branched fatty acid and a long chain branched alcohol;
c) a long chain fatty acid; and
d) a long chain alcohol.

According to a third aspect of the present invention, there is provided the use of a blend according to the first or second aspect of the present invention in a moisturising formulation for moisturising skin.

According to a fourth aspect of the present invention, there is provided a blend according to the first or second aspect of the present invention for topical application to the skin or mucosa having an improved water vapour transmission rate.

According to a fifth aspect of the present invention, there is provided a pastillated and/or flaked product comprising a blend according to either the first or the second aspect of the present invention.

According to a sixth aspect of the present invention, there is provided an oil-in-water emulsion, wherein the oil phase comprises a blend according to either the first or the second aspect of the present invention.

The blend of the first or second aspect of the present invention is preferably present in an emulsion according to the sixth aspect of the present invention in the range from 0.1 to 10%, preferably 0.5 to 8%, more preferably 1 to 7%, particularly 2 to 6%, and especially 3 to 5.5%, by weight of the total emulsion. Desirably, the blend is present in the emulsion at a concentration of 5% by weight of the total emulsion.

The emulsion may comprise additional components, for example, additional emollients, carriers, surfactants and the like.

Any additional emollients in the emulsion of the present invention will preferably mainly be an emollient oil of the type used in personal care or cosmetic products. The emollient can and usually will be an oily material which is liquid at ambient temperature. Alternatively it can be solid at ambient temperature, in which case in bulk it will usually be a waxy solid, provided it is liquid at an elevated temperature at which it can be included in and emulsified in the composition. The manufacture of the composition preferably uses temperatures up to 100° C., more preferably about 80° C., and therefore such solid emollients will preferably have melting temperatures of less than 100° C., and more preferably less than 70° C.

Suitable normally liquid emollient oils include non-polar oils, for example mineral or paraffin, especially isoparaffin, oils, such as that sold by Croda as Arlamol (trade mark) HD; or medium polarity oils, for example vegetable ester oils such as jojoba oil, vegetable glyceride oils, animal glyceride oils, such as that sold by Croda as Crodamol (trade mark) GTCC (caprylic/capric triglyceride), synthetic oils, for example synthetic ester oils, such as isopropyl palmitate and those sold by Croda as Crodamol IPM and Crodamol DOA, ether oils, particularly of two fatty e.g. C8 to C18 alkyl residues, such as that sold by Cognis as Cetiol OE (dicapryl ether), guerbet alcohols such as that sold by Cognis as Eutanol G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by Croda as Arlamol PS15 (propoxylated stearyl alcohol). Suitable emollient materials that can be solid at ambient temperature but liquid at temperatures typically used to make the compositions of this invention include jojoba wax, tallow and coconut wax/oil.

Mixtures of emollients can be used, and in some cases solid emollients may dissolve wholly or partly in liquid emollients or in combination the freezing point of the mixture may be suitably low. Where the emollient composition is a solid (such as fatty alcohols) at ambient temperature, the resulting dispersion may technically not be an emulsion (although in most cases the precise phase of the oily disperse phase cannot readily be determined) but such dispersions behave as if they were true emulsions and the term emulsion is used herein to include such compositions.

The amount of water present in the emulsion is suitably greater than 5%, preferably in the range from 30 to 90%, more preferably 50 to 90%, particularly 70 to 85%, and especially 75 to 80% by weight of the total composition.

The water phase may include a polyol, e.g. glycerin. In this case, the total water phase including the polyol present in the emulsion is suitably greater than 5%, preferably in the range from 30 to 90%, more preferably 50 to 90%, particularly 70 to 85%, and especially 75 to 80% by weight of the total composition.

The emulsion may further comprise cholesterol as an additional moisturisation component. When present, the cholesterol is present at an amount of 0.1 to 5% by weight of the total emulsion.

The emulsions according to the present invention may also contain other additional surfactant materials which form part of the emulsifier system. Other suitable surfactants include relatively hydrophilic surfactants, e.g. having a HLB value of greater than 10, preferably greater than 12, and relatively hydrophobic surfactants e.g. having a HLB value of less than 10, preferably less than 8. Relatively hydrophilic surfactants include alkoxylate surfactants with an average in the range from about 10 to about 100 alkylene oxide, particularly ethylene oxide residues; and relatively hydrophobic surfactants include alkoxylate surfactants preferably with an average in the range from about 3 to about 10 alkylene oxide, particularly ethylene oxide residues.

Personal care or cosmetic emulsions can be divided by viscosity into milks and lotions, which preferably have a low shear viscosity (measured at shear rates of about 0.1 to 10 $s^{-1}$ as is typically used in Brookfield viscometers) of up to 10,000 mPa·s, and creams which preferably have a low shear viscosity of more than 10,000 mPa·s.

Milks and lotions preferably have a low shear viscosity in the range from 100 to 10,000, more preferably 200 to 5,000, and particularly 300 to 1,000 mPa·s. The amount of surfactant composition according to the present invention present in a milk or lotion is preferably in the range from 2 to 3% by weight of the total composition.

Creams preferably have a low shear viscosity of at least 20,000, more preferably in the range from 30,000 to 80,000, and particularly 40,000 to 70,000 mPa·s, although even higher viscosities e.g. up to about $10^6$ mPa·s, may also be used. The amount of surfactant composition present in a cream is preferably in the range from 4 to 5.5% by weight of the total composition.

The emulsions of the invention may be made by conventional emulsification and mixing methods. For example, the surfactant composition may be added to (i) the oil phase, which is then added to the aqueous phase, or (ii) both the combined oil and water phases, or (iii) the water phase, which is then added to the oil phase. Method (iii) is preferred. In all of these methods, the resulting mixture can then be emulsified using standard techniques. It is preferred to either heat the aqueous and oil phases usually above about 60° C., e.g. to about 80 to 85° C., or to subject the aqueous phase to high intensity mixing at lower, e.g. about ambient, temperature. Vigorous mixing and the use of moderately elevated temperatures can be combined if desired. The heating and/or high intensity mixing can be carried out before, during or after addition of the oil phase but once emulsified, care should be taken not to destroy the liquid crystal system by excessive mixing or stirring.

The emulsions can also be made by inverse emulsification methods, whereby the surfactant composition is added to either the oil phase or the aqueous phase, and the aqueous phase is mixed into the oil phase to initially form a water in oil emulsion. Aqueous phase addition is continued until the system inverts to form an oil in water emulsion. Plainly a substantial amount of aqueous phase will generally be needed to effect inversion and so this method is not likely to be used for high oil phase content emulsions. Vigorous mixing and the use of moderately elevated temperatures can be combined if desired. Heating can be carried out during or after addition of the aqueous phase and before, during or after inversion. High intensity mixing can be carried out during or after addition of the aqueous phase, and before or during inversion The emulsions may for example be microemulsions or nanoemulsions, having a mean droplet size over a wide range, preferably in the range from 10 to 10,000 nm. In one embodiment, the emulsion droplet size may be reduced, for example by high pressure homogenisation, preferably to a value in the range from 100 to 1,000 nm, more preferably 300 to 600 nm.

The emulsions according to the present invention are preferably stable for greater than one month, more preferably greater than two months, particularly greater than three months, and especially greater than four months at ambient temperature (23° C.), and also preferably at 40° C. The stability at even higher temperatures can be particularly important, and therefore the emulsion is preferably stable for greater than one week, preferably greater than two weeks, more preferably greater than 3 weeks, particularly greater than one month, and especially greater than two months at 50° C.

Many other components may be included in the emulsions to make personal care or cosmetic compositions or products. These components can be oil soluble, water soluble or non-soluble. Examples of such materials include:

(i) preservatives such as those based on parabens (alkyl esters of 4-hydroxybenzoic acid), phenoxyethanol, substituted ureas and hydantoin derivatives e.g. those sold commercially under the trade names Germaben II Nipaguard BPX and Nipaguard DMDMH, when used preferably at a concentration in the range from 0.5 to 2% by weight of the total composition;

(ii) perfumes, when used preferably at a concentration in the range from 0.1 to 10% more preferably up to about 5%, and particularly up to about 2% by weight of the total composition;

(iii) humectants or solvents such as alcohols, polyols such as glycerol and polyethylene glycols, when used preferably at a concentration in the range from 1 to 10% by weight of the total composition;

(iv) sunfilter or sunscreen materials including organic sunscreens and/or inorganic sunscreens including those based on titanium dioxide or zinc oxide; when used preferably at a concentration in the range from 0.1% to 20%, more preferably 1 to 15%, and particularly 2 to 10% by weight of the total composition;

(v) alpha hydroxy acids such as glycolic, citric, lactic, malic, tartaric acids and their esters; self-tanning agents such as dihydroxyacetone, and beta hydroxyl acids such as salicylic acid and their esters;

(vi) anti-aging, cell-turnover-improving, and antimicrobial, particularly anti-acne, components such as salicylic acid;

(vii) vitamins and their precursors including: (a) Vitamin A, e.g. as retinyl palmitate and other tretinoin precursor molecules, (b) Vitamin B, e.g. as panthenol and its derivatives, (c) Vitamin C, e.g. as ascorbic acid and its derivatives, (d) Vitamin E, e.g. as tocopheryl acetate, (e) Vitamin F, e.g. as polyunsaturated fatty acid esters such as gamma-linolenic acid esters;

(viii) skin care agents such as ceramides either as natural materials or functional mimics of natural ceramides;

(ix) phospholipids, such as synthetic phospholipids or natural phospholipids, eg lecithin;

(x) vesicle-containing formulations;

(xi) botanical extracts with beneficial skin care properties;

(xii) skin whiteners such as ODA White (trade mark) sold by Sederma, a member of Croda International Plc kojic acid, arbutin and similar materials;

(xiii) skin repair compounds actives such as Allantoin and similar series;

(xiv) caffeine and similar compounds;

(xv) cooling additives such as menthol or camphor;

(xvi) insect repellents such as N,N-diethyl-3-methylbenzamide (DEET) and citrus or eucalyptus oils;

(xvii) essential oils;

(xviii) ethanol; and (xix) pigments, including microfine pigments, particularly oxides and silicates, e.g. iron oxide, particularly coated iron oxides, and/or titanium dioxide, and ceramic materials such as boron nitride, or other solid components, such as are used in make up and cosmetics, to give suspoemulsions, preferably used in an amount in the range from 1 to 15%, more preferably at least 5% and particularly approximately 10%.

The composition and emulsions according to the present invention are suitable for use in a wide range of compositions and end-use applications, such as moisturizers, sunscreens, after sun products, body butters, gel creams, high perfume containing products, perfume creams, baby care products, hair conditioners, skin toning and skin whitening products, water-free products, anti-perspirant and deodorant products, tanning products, cleansers, 2-in-1 foaming emulsions, multiple emulsions, preservative free products, emulsifier free products, mild formulations, scrub formulations e.g. containing solid beads, silicone in water formulations, pigment containing products, sprayable emulsions, colour cosmetics, conditioners, shower products, foaming emulsions, make-up remover, eye make-up remover, and wipes.

Formulations containing a composition or emulsion according to the present invention may have a pH value over a wide range, preferably in the range from 3 to 13, more preferably 4 to 9, and especially 5 to 6.

The present invention further extends to a method of moisturising skin, the method comprising:
 a) forming a blend comprising an ester of a long chain branched fatty acid and a long chain branched alcohol and a dialkyl amphiphilic component;
 b) forming an oil-in-water emulsion wherein the oil phase comprises the blend; and
 c) applying the oil-in-water emulsion to the skin.

The features of the present invention may be taken in any combination and with any aspect of the invention.

EXAMPLES

The invention is illustrated by the following non-limiting examples. All parts and percentages are given by weight of the total composition unless otherwise stated.

Example 1

Production of Emulsion

Test emulsion formulation A, formulation B, and comparative formulation X were produced from the components listed below in Table 1.

TABLE 1

Emulsion compositions

| Phase | Component | Formulation A - test emulsion (% w/w) | Formulation B - test emulsion (% w/w) | Formulation X - comparative emulsion (% w/w) |
|---|---|---|---|---|
| A | Blend (pastilles) | 5.0 | 5.0 | 0.0 |
| A | Mineral oil | 0.0 | 0.0 | 5.0 |
| A | Glyceryl stearate (Cithrol GMS 40 (N/E 0400 Ph Eur)) | 1.2 | 1.2 | 1.2 |
| A | Ceteareth-20 (Brij CS20 (Volpo CS20)) | 0.4 | 0.4 | 0.4 |
| A | Isohexadecane (Arlamol HD ex CRODA) | 5.0 | 5.0 | 5.0 |
| A | PPG-15 stearyl ether (Arlamol PS15E ex CRODA) | 4.0 | 4.0 | 4.0 |
| A | Dimethicone (Dow Corning 200 100 cst) | 1.0 | 1.0 | 1.0 |
| A | Propylparaben | 0.5 | 0.5 | 0.5 |
| B | Water | 68.2 | 68.2 | 68.2 |
| B | Methylparaben | 0.15 | 0.15 | 0.15 |
| B | Glycerin (Pricerine 9091 ex CRODA) | 5.0 | 5.0 | 5.0 |
| B | Acrylates/C10-30 alkyl acrylate crosspolymer (2% w/w solution) (OptaSense G82 ex CRODA) | 10.0 | 10.0 | 10.0 |

To form the emulsions, first pastilles comprising the blend of the present invention were formed. The pastilles for Formulation A were formed by combining 22.5% w/w isostearyl isostearate (Crodamol ISIS ex CRODA), 18% w/w potassium dicetyl phosphate, 22.5% w/w behenic acid and 37% w/w cetyl alcohol (Crodacol C90 ex CRODA) to form the blend. This was neutralized with potassium hydroxide, the residual water removed and the blend pastillated to form the pastilles. The pastilles for Formulation B were formed by combining 22.5% w/w isostearyl isostearate (Crodamol ISIS ex CRODA), 18% w/w potassium dicetyl phosphate, 22.5% w/w stearic acid and 37% w/w cetyl alcohol (Crodacol C90 ex CRODA) to form the blend. This was neutralized with potassium hydroxide, the residual water removed and the blend pastillated to form the pastilles. The pastilles of the blend were then added to the remaining phase A components and heated to above 75° C. in a water bath and mixed together until uniform to form the oil phase (A) of the emulsions.

In a separate vessel, the phase B components (aqueous phase) were mixed and heated in a water bath to above 75° C.

The phase A mixture was slowly added to the phase B mixture while stirring at approximately 300 rpm, and homogenised for 1 minute using an Ultra-Turrax® disperser stirring at approximately 11000 rpm.

The resulting emulsion was then cooled to room temperature whilst gently stirring at approximately 150 rpm.

The pH of the resulting mixture was then checked and modified to between 5 and 5.5 using potassium hydroxide.

Example 2

In-Vitro Assessment of Water Vapour Transmission Rate (WVTR) at 50% controlled humidity and a temperature of 21° C.

Formulations A and X were produced according to the method described in Example 1.

WVTR testing was carried out on both the emulsions separately in a controlled humidity room 50% RH±5, 21° C.±1.

1. A uniform film (5×6 cm) of test emulsion was drawn down onto a section (7×6 cm) of Vitro-Corneum™ (IMS Inc., Portland Me., U.S.A.) using a draw down bar (Sheen bird type applicator) with a 50 micron gap size and impression bed (Sheen Instruments Ltd., Surrey, England).

2. Once films had been applied Vitro-corneum section were placed on mesh shelves (IMS Inc., Portland Me., U.S.A.) and dried in a 40° C. oven for 1 h prior to application of a second coat on top of the first using the same method as above.
3. Samples were then left to dry in the controlled humidity room for 24 hours.
4. To ensure a uniform film thickness of the emulsion residual films, each section of Vitro-corneum was weighed before application and after 24 hours.
5. The Vitro-corneum was then attached to a WVTR chamber containing 5 ml of water and allowed to equilibrate for 1 h prior to testing. The surface area of attached vitro-corneum was 11.34 cm$^2$.
6. The WVTR was then determined gravimetrically using a five point balance (AB135-S Mettler-Toledo Ltd., Leicester, England) by weighing at the beginning of the experiment ($W_0$) after 1 h ($W_1$), 2 h ($W_2$), 3 h ($W_3$) and 24 h ($W_{24}$).

The results are shown in Table 2. As can be seen the test emulsion, formulation A, significantly outperformed the comparative emulsion, formulation X, in reducing the flux.

TABLE 2

Water Vapour Transmission Rate (WVTR) 50% RH & 21° C.

| Time (min) | Formulation A (test emulsion) sample 1 | Formulation A (test emulsion) sample 2 | Formulation A (test emulsion) sample 3 | Weight loss (g h$^{-1}$) | | | WVTR (g m$^{-2}$ h$^{-1}$) | | | Av. WVTR (g m$^{-2}$ h$^{-1}$) | Standard deviation | Students t-test formulation A vs. X (p value) |
|---|---|---|---|---|---|---|---|---|---|---|---|---|
| 0 | 6.84072 | 6.87452 | 6.85022 | | | | | | | | | |
| 60 | 6.79805 | 6.83118 | 6.80930 | 0.04267 | 0.04334 | 0.04092 | 37.62787 | 38.21869 | 36.08466 | 37.31041 | 1.10187 | 0.000028 |
| 120 | 6.75483 | 6.78744 | 6.76808 | 0.04322 | 0.04374 | 0.04122 | 38.11287 | 38.57143 | 36.34921 | 37.67784 | 1.17325 | 0.000021 |
| 180 | 6.71246 | 6.74460 | 6.72779 | 0.04237 | 0.04284 | 0.04029 | 37.36332 | 37.77778 | 35.52910 | 36.89006 | 1.19671 | 0.000040 |
| 1440 | 5.89959 | 5.90794 | 5.94964 | 0.03921 | 0.04027 | 0.03752 | 34.58003 | 35.51514 | 33.09009 | 34.39509 | 1.22305 | 0.000034 |

| Time (min) | Formulation X (comparative emulsion) sample 1 | Formulation X (comparative emulsion) sample 2 | Formulation X (comparative emulsion) sample 3 | Weight loss (g h$^{-1}$) | | | WVTR (g m$^{-2}$ h$^{-1}$) | | | Av. WVTR (g m$^{-2}$ h$^{-1}$) | Standard deviation |
|---|---|---|---|---|---|---|---|---|---|---|---|
| 0 | 6.78481 | 6.77973 | 6.73462 | | | | | | | | |
| 60 | 6.72273 | 6.71941 | 6.67352 | 0.06208 | 0.06032 | 0.06110 | 54.74427 | 53.19224 | 53.88007 | 53.93890 | 0.77768 |
| 120 | 6.66073 | 6.65832 | 6.61167 | 0.06200 | 0.06109 | 0.06185 | 54.67372 | 53.87125 | 54.54145 | 54.36214 | 0.43024 |
| 180 | 6.59908 | 6.59859 | 6.55115 | 0.06165 | 0.05973 | 0.06052 | 54.36508 | 52.67196 | 53.36861 | 53.46855 | 0.85097 |
| 1440 | 5.42917 | 5.44446 | 5.38431 | 0.05649 | 0.05564 | 0.05626 | 49.81041 | 49.06195 | 49.61456 | 49.49564 | 0.38814 |

Example 3

In-Vitro Assessment of WVTR at High and Low Humidity

After the WVTR testing of Example 2 carried out in the humidity controlled room test emulsion formulation A and comparative emulsion formulation X were tested again at low and high humidity. The samples were individually weighed every minute and placed into a humidity controlled box on a mesh shelf at 30% RH and 32° C. for one hour before being re-weighed to calculate flux. 32° C. corresponds approximately to skin surface temperature.

The results are shown in Table 3. As can be seen from Table 3 a lower humidity and higher temperature increased the flux. In this test, the test emulsion, formulation A, reduced the flux by approximately 50%, and by a much greater extent than the comparative emulsion, formulation X.

TABLE 3

Water Vapour Transmission Rate (WVTR) 30% RH & 32° C.

| Time (min) | Formulation A (test emulsion) sample 1 | Formulation A (test emulsion) sample 2 | Formulation A (test emulsion) sample 3 | Weight loss (g h$^{-1}$) | | | WVTR (g m$^{-2}$ h$^{-1}$) | | | Av. WVTR (g m$^{-2}$ h$^{-1}$) | Standard deviation | Students t-test formulation A vs. X (p value) |
|---|---|---|---|---|---|---|---|---|---|---|---|---|
| 0 | 5.82816 | 5.83482 | 5.88003 | | | | | | | | | |
| 60 | 5.74752 | 5.75115 | 5.80383 | 0.08064 | 0.08367 | 0.07620 | 71.11111 | 73.78307 | 67.19577 | 70.69665 | 3.31315 | 0.000006 |

TABLE 3-continued

Water Vapour Transmission Rate (WVTR) 30% RH & 32° C.

| Time (min) | Formulation X (comparative emulsion) sample 1 | Formulation X (comparative emulsion) sample 2 | Formulation X (comparative emulsion) sample 3 | Weight loss (g h$^{-1}$) | | | WVTR (g m$^{-2}$ h$^{-1}$) | | | Av. WVTR (g m$^{-2}$ h$^{-1}$) | Standard deviation |
|---|---|---|---|---|---|---|---|---|---|---|---|
| 0 | 5.33644 | 5.34742 | 5.28633 | | | | | | | | |
| 60 | 5.18300 | 5.19038 | 5.13120 | 0.15344 | 0.15704 | 0.15513 | 135.30864 | 138.48325 | 136.79894 | 136.86361 | 1.58829 |

After testing the samples at low humidity samples were then tested at high humidity, 90% RH and 32° C.

The results from the higher humidity tests are shown in Table 4. The flux was slightly reduced at the elevated humidity even though the temperature was increased. However, as can be seen from Table 4, the test emulsion, formulation A, still outperformed the comparative emulsion, formulation X.

TABLE 4

Water Vapour Transmission Rate (WVTR) 90% RH & 32° C.

| Time (min) | Formulation A (test emulsion) sample 1 | Formulation A (test emulsion) sample 2 | Formulation A (test emulsion) sample 3 | Weight loss (g h$^{-1}$) | | | WVTR (g m$^{-2}$ h$^{-1}$) | | | Av. WVTR (g m$^{-2}$ h$^{-1}$) | Standard deviation | Students t-test formulation A vs. X (p value) |
|---|---|---|---|---|---|---|---|---|---|---|---|---|
| 0 | 5.86672 | 5.87095 | 5.91437 | | | | | | | | | |
| 60 | 5.82816 | 5.83482 | 5.88003 | 0.03287 | 0.03699 | 0.03527 | 28.98589 | 32.61905 | 31.10229 | 30.90241 | 1.82481 | 0.004309 |

| Time (min) | Formulation X (comparative emulsion) sample 1 | Formulation X (comparative emulsion) sample 2 | Formulation X (comparative emulsion) sample 3 | Weight loss (g h$^{-1}$) | | | WVTR (g m$^{-2}$ h$^{-1}$) | | | Av. WVTR (g m$^{-2}$ h$^{-1}$) | Standard deviation |
|---|---|---|---|---|---|---|---|---|---|---|---|
| 0 | 5.42917 | 5.44446 | 5.38431 | | | | | | | | |
| 60 | 5.38172 | 5.39309 | 5.32786 | 0.04745 | 0.05137 | 0.05645 | 41.84303 | 45.29982 | 49.77954 | 45.64080 | 3.97923 |

Example 4

Moisture Efficacy Test (MET)—Clinical Study

A dry skin clinical study was arranged with University of Medunsa School of Pharmacy in South Africa, an internationally recognised product testing laboratory. The aim was to assess the effect of twice daily application of test emulsion, formulation A, and comparative emulsion, formulation X, (the 'test products') for moisturisation performance when applied to the outer, lower leg of female subjects. Twenty five panellists completed the study all of whom were healthy females. The study lasted for 25 days; a 7 day dry-out period (week −1), 14 day treatment period (weeks 1 and 2), and a 4 day regression period (week 3).

Product Application/Use

1) Dry-Out Period

The panellists were instructed to wash their legs 2-4 times daily using a Dove sensitive skin soap bar in order to induce skin dryness, and not to apply any products to the test sites.

2) Treatment Period

The panellists were instructed to continue washing their legs twice daily throughout the treatment phase in order to continually induce skin dryness. Panellists had to attend assessment visits at the study centre at specific times on week days during weeks 1 and 2. Panellists had to apply the test products to test sites after an assessment visit on Monday, Wednesday and Friday of weeks 1 and 2; assessment took place 2.5 hrs after the first wash of the test sites on those days.

The application of the test products involved a quantity of 0.2 g of each of formulations A and B being applied on the appropriate test site twice a day by the panellist using a 1 ml tuberculin syringe (needle-less). Initial product application was supervised by study staff for several days until panellist competency was assured.

3) Regression Period

On Monday of week three, products were returned by the panellists and no application of the test products took place. Panellists were instructed to continue to wash their legs twice a day and to attend assessment visits at the study centre at specific times each day.

Treatment Assignment and Test Sites

The test emulsion, formulation A, the comparative emulsion, formulation X, and an untreated control site were assigned to the test sites for each subject as per a rotational randomization schedule.

Test sites were located on the panellists' lower leg (outer lateral aspect in the area extending from above the ankle to below the knee). The test sites were approximately 20 cm$^2$ (6.7 cm×3 cm), with a 4 cm gap between sites.

Visual Assessment

Visual evaluations were performed by a trained visual evaluator using a 2× magnifying lamp. Evaluations were performed before and after treatment with test products. Visual evaluations were graded on a scale of 0-5 (see Table 5 below).

TABLE 5

Visual evaluation grading scale

| Grade | Dryness Scale |
|---|---|
| 0.0 | Smooth, no evidence of dryness. |
| 1.0 | Slightly dry skin, occasional scale, not necessarily uniformly distributed. |
| 2.0 | Moderately dry skin, fairly uniformly distributed scale, but no wide spread uplifting and flaking. |
| 3.0 | Severely dry skin, pronounced scaling visible to the naked eye, definite uplifting of edges or scale sections surface may have a whitish appearance. |
| 4.0 | Extremely dry skin, extensive scaling and pronounced separation of scale edges, some evidence of cracking. |
| 5.0 | Extremely dry skin with deep or extensive cracking and evidence of bleeding. |

Whole number scores reflect generalized condition; half number scores were used to represent an intermediate condition or less than 50% of the test area having the next highest scoring condition.

Results

The scores for the average net change in visual dryness from the baseline dryness observed on Day 1 for the test emulsion, formulation A, the comparative emulsion, formulation X, and an untreated control site for the treatment and regression periods of the study are given in Table 6 below.

TABLE 6

MET Average Net Change in Visual Dryness Score

| | Day 3 | Day 5 | Day 8 | Day 10 | Day 12 | Day +1 | Day +2 | Day +3 | Day +4 |
|---|---|---|---|---|---|---|---|---|---|
| *Formulation A - test emulsion* | | | | | | | | | |
| Av. Net Change | −0.160 | −0.660 | −1.068 | −1.591 | −1.840 | −1.640 | −1.800 | −1.780 | −1.600 |
| Std. | 0.608 | 0.863 | 0.849 | 0.734 | 0.800 | 0.670 | 0.722 | 0.678 | 0.750 |
| Conf. | 0.238 | 0.338 | 0.333 | 0.288 | 0.314 | 0.262 | 0.283 | 0.266 | 0.294 |
| *Formulation X - comparative emulsion* | | | | | | | | | |
| Av. Net Change | −0.280 | −0.340 | −0.750 | −1.341 | −1.380 | −1.320 | −1.200 | −1.080 | −1.080 |
| Std. | 0.522 | 0.932 | 0.768 | 0.892 | 0.869 | 0.762 | 0.707 | 0.746 | 0.799 |
| Conf. | 0.205 | 0.365 | 0.301 | 0.349 | 0.341 | 0.299 | 0.277 | 0.292 | 0.313 |
| *Untreated* | | | | | | | | | |
| Av. Net Change | 0.360 | 0.300 | 0.318 | 0.136 | 0.020 | 0.240 | 0.340 | 0.220 | 0.340 |
| Std. | 0.468 | 0.612 | 0.628 | 0.727 | 0.757 | 0.614 | 0.572 | 0.647 | 0.624 |
| Conf. | 0.184 | 0.240 | 0.246 | 0.285 | 0.297 | 0.241 | 0.224 | 0.254 | 0.245 |

A statistical analysis using the Wilcoxon matched-pairs signed-ranks test as a non-parametric equivalent of the two-sample paired t-test is given below in Table 7.

TABLE 7

MET Visual Assessment Statistical Analysis of Test Emulsion, formulation A, vs. Comparative Emulsion, formulation B (14 day treatment period - days 1 to 14 - followed by 4 day regression period - days +1 to +4).

| | Day 3 | Day 5 | Day 8 | Day 10 | Day 12 | Day +1 | Day +2 | Day +3 | Day +4 |
|---|---|---|---|---|---|---|---|---|---|
| *Formulation A - test emulsion* | | | | | | | | | |
| Formulation X - comparative emulsion | 0.45860 | 0.13960 | 0.12050 | 0.28130 | 0.02041 | 0.07921 | 0.00143 | 0.00123 | 0.01362 |
| Untreated | 0.00422 | 0.00006 | 0.00000 | 0.00006 | 0.00003 | 0.00002 | 0.00001 | 0.00002 | 0.00001 |

As can be seen from Tables 6 and 7, test formulation A was seen to significantly relieve dry skin to a greater extent compared to the comparative formulation X in both the treatment and regression phase of the study. Therefore, it can be concluded that test formulation A had significantly enhanced moisturising effect in both the treatment and regression phases of the study.

Example 5

Assessment of Sensory Attributes of Formulations A and X

The aim of the usage study is to gain an understanding of what sensory attributes the moisturiser complex adds to an emulsion using an untrained in-house panel.

Panellists were instructed to apply two different moisturisers, one to each side of the face as part of their normal daily routine, twice a day morning and night for one week. The moisturisers were test emulsion, formulation A, and comparative emulsion, formulation X. Panellists were required to complete a short questionnaire before starting the study and then again at the end after a week of application.

Panellists were simply asked to substitute or incorporate the test moisturisers into their normal daily routine and therefore the use of make-up was still permitted. Panellists were asked not use any other moisturiser on the face for 2 days prior to or throughout the duration of the study.

Samples were assigned a three digit randomised code and assigned to individual panellists indicating which side of the face to apply. The side of the face that each sample was assigned was alternated between panellists.

Panellists were informed that there was 12 g of moisturiser in each pump bottle; enough for 2-3 pumps to each side of the face morning and night for 7 days. 1 pump=~0.18 g.

Pre-Study Questionnaire

The use of a pre-study questionnaire allowed for calculation of percentage change before and after application. Panellists were asked to rate how smooth, soft, radiant and oily they thought their skin felt on a 1 to 10 scale.

Post-Study Questionnaire

Panellists were asked again to rate how smooth, soft, radiant and oily they thought their skin felt on a 1 to 10 scale. Panellists were also asked to indicate which moisturiser they preferred.

Statistical Analysis

Non-parametric, Wilcoxon matched-pairs signed-ranks test was used to analyse the results. The results are given as the variance, or p value.

Results

Preference

71% of panellists preferred the test emulsion, formulation A (22 panellists out of 31).

Comparison Between Formulations A and X after One Week of Application

For smoothness, radiance, softness and oiliness it was possible to calculate the percentage change before and after one week application.

After one week of application the 35% increase in smoothness recorded for formulation A was significantly better, at a 95% confidence level, in comparison to the 23% for formulation X p=0.0273.

For radiance the 31% increase for formulation A was significantly better at a 90% confidence level, in comparison to 26% for formulation X p=0.0674.

For softness the 26% increase for formulation A was not significant in comparison to 24% for formulation X p=0.4549.

For oiliness the 8% increase for formulation A was not significant in comparison to the 6% for formulation X p=0.5781.

Example 6

2D Wide- and Small-Angle X-Ray Scattering Analysis (WAXS and SAXS)

Test emulsion, formulation A, and comparative emulsion, formulation X, were made according to the method of Example 1 above.

Six samples were then prepared, three each using formulations A and X as described in Table 8 below.

TABLE 8

Samples prepared for x-ray scattering analysis

| Formulation | Dried for 1 hr at ambient pressure, on a 32° C. block | Dried for >6 hrs in vacuum jar | No 'drying' at all |
|---|---|---|---|
| X | B1 | B2 | B3 |
| A | A1 | A2 | A3 |

The six samples were analysed in x-ray cells containing polyimide windows. 2-D wide- and small-angle x-ray scattering patterns were obtained from each sample. To prepare the x-ray cells, 2 ml of a sample was put into an x-ray cell with a silicone rubber spacer (1 mm deep) and polyimide windows using a spatula. The cell was then sealed with double-sided sticky tape, and clamped into a metal cell. The prepared cell was loaded into an evacuated chamber in the x-ray instrument (Nanostar). Each cell was exposed to an x-ray beam from the x-ray instrument for 900 s. Small-angle scattering patterns were obtained on a digital Vantek detector, and wide-angle scattering patterns were obtained on an image plate. "Background" wide- and small-angle scattering patterns from an empty cell (the polyimide windows) were also obtained. The wide-angle scattering analysis looked at scattering that occurred between 0° and 40° from the x-ray beam. The small-angle scattering analysis looked at scattering that occurred between 0° and 5° from the x-ray beam.

Radial averaging was performed on each 2-D x-ray scattering pattern to produce single profiles for each sample for each of the wide- and small-angle x-ray scattering tests. Each scattered ring seen on a 2-D scattering pattern resulted in a peak on the profile. The profiles from the six samples are plotted in FIGS. 1 and 2.

Results

Comparative Emulsion, Formulation X

In the WAXS scattering patterns for samples B1 to B3 (FIG. 1), a peak is seen at approximately 5° which arises from the polyimide windows (see background sample). The dried samples, B1 and B2, showed peaks at approximately 18° and 22° which correspond to the peaks shown by liquid and orthorhombic phases of an emulsion. B3 shows a peak at around 30° which indicates the presence of water and dilutes any other peaks.

Figure 2:
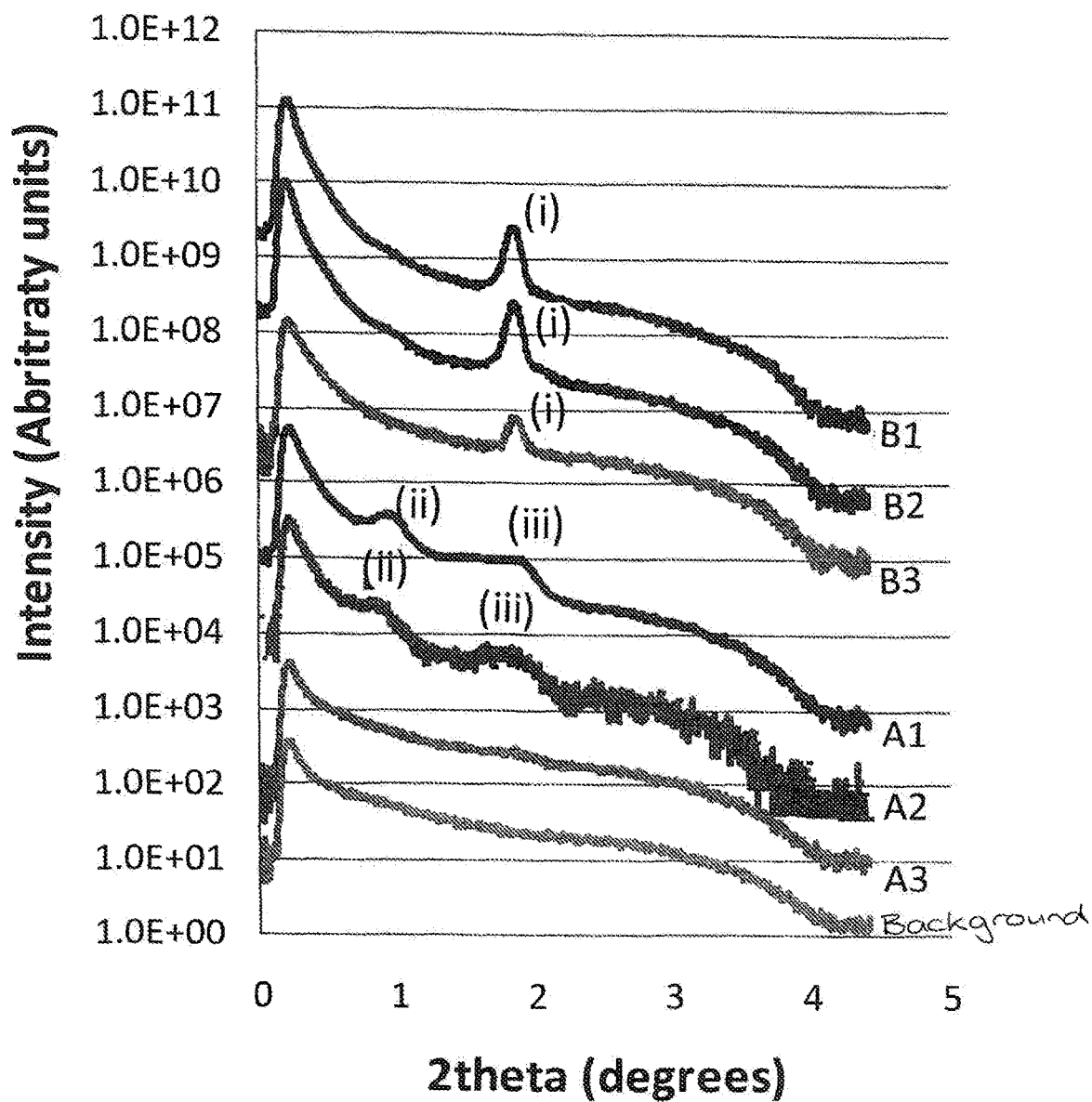
FIG. 2 shows small angle x-ray scattering patterns for comparative emulsions and test emulsions.

All of the SAXS scattering patterns from samples B1 to B3 have a prominent peak at 5.0 nm ((i) in FIG. 2), with no significant change in this dimension on drying. This pattern indicates a first reflection of a lamellar structure having a repeat distance of 5 nm.

Test Emulsion, Formulation A

In the WAXS scattering patterns (FIG. 1), a peak is seen at approximately 5° for each of A1 to A3, which arises from the polyimide windows (see background sample). The dried samples, A1 and A2, showed prominent peaks at approximately 21° and 23° which is characteristic of tight packing of molecules within the sample, i.e. where the head groups of the molecules are positioned close together. A3 shows the same peaks, albeit diluted due to the presence of water, as well as the peak at around 30° which indicates the presence of water.

For the SAXS scattering patterns (FIG. 2), in the dried Formulation A samples (A1 and A2), instead of a sharp reflection at 5.0 nm, there are two broader reflections at approximately 10 nm ((ii) in FIG. 2) and 5 nm ((iii) in FIG. 2). These reflections are the $1^{st}$ and $2^{nd}$ order reflections of a periodic stack of bilayers (each bilayer having a lamellar structure), this time with spacing 10 nm. The results indicate that the higher periodic spacing in samples A1 and A2 as compared with B1 to B3 are due to the presence of a thicker bilayer in the test emulsion samples.

In the hydrated sample, A3, these peaks can't be seen. However, the reduction in signal intensity due to the lower concentration of surfactant formulation relative to water means that these two reflections, although still present, are too weak to see.

The results of the WAXS and SAXS analysis provide evidence of lamellar type packing in the comparative emulsion, formulation X, but in the test emulsion, formulation A, there was evidence of the formation of liquid crystals and a much thicker stack of lamellar layers than formulation X, with a 10 nm spacing and a tighter orthorhombic packing state. Furthermore, it is shown that the lamellar layer is formed upon drying with the test emulsion as opposed to the comparative emulsion where the lamellar layer is present in the hydrated emulsion sample as well as the dried samples. Therefore, the test emulsion provides a structured residual phase which is left on the skin during drying of the emulsion. It is this property of the test emulsion that replenishes the functionality of diminished skin lipids which is more prevalent in dry skin.

The present invention provides a matrix of materials that mimics the mechanism of the intercellular lipid matrix in the stratum corneum of the skin, in that it provides a structured residual oil phase on the surface of the skin from an oil-in-water emulsion after evaporation of the water. The residual oil phase reduces the dryness of the skin by providing a water permeation barrier on the skin's surface, and also by providing a moisturisation effect by internal occlusion within the stratum corneum. The present invention therefore provides a product having an increased moisturisation effect.

Any or all of the disclosed features, and/or any or all of the steps of any method or process described, may be combined in any combination.

Each feature disclosed herein may be replaced by alternative features serving the same, equivalent or similar purpose. Therefore, each feature disclosed is one example only of a generic series of equivalent or similar features.

The above statements apply unless expressly stated otherwise. The term specification, for these purposes, includes the description and any accompanying claims, abstract and drawings.

The invention claimed is:

1. A blend for a moisturisation formulation comprising:
   a) at least one anionic dialkyl amphiphilic component, wherein each alkyl group therein is independently selected from the group consisting of C10 to C30 alkyl groups, and the anionic functionality is provided by a phosphorus acid group or salt thereof or a sulfur acid group or salt thereof; and
   b) at least one ester of a C12 to C30 branched fatty acid and a C12 to C30 branched alcohol;
   wherein the anionic dialkyl amphiphilic component is present in the blend at a concentration of between 10 to 75% by weight of the total blend, and wherein the blend is not an emulsion.

2. The blend of claim 1, wherein the anionic dialkyl amphiphilic component has a packing parameter, R, of between 0.25 and 1.25.

3. The blend of claim 1, wherein the anionic dialkyl amphiphilic component is a dialkyl phosphate.

4. The blend of claim 1, wherein the C12 to C30 branched fatty acid and the C12 to C30 branched alcohol in the ester are alkyl branched.

5. The blend of claim 1, wherein the blend additionally comprises a long chain fatty acid or a salt thereof.

6. The blend of claim 1, wherein the ester is an ester of a C18 mono- and/or poly-branched fatty acid and a C18 mono- and/or poly-branched alcohol.

7. The blend of claim 5, wherein the long chain fatty acid is a C12 to C32 fatty acid.

8. The blend of claim 1, wherein the blend additionally comprises a long chain alcohol.

9. The blend of claim 8, wherein the long chain alcohol is a C12 to C28 alcohol.

10. A pastillated and/or flaked product comprising the blend of claim 1.

11. The blend of claim 1, further comprising
    c) a long chain fatty acid; and
    d) a long chain alcohol.

12. The blend of claim 11 wherein the blend consists of components a), b), c), and d).

13. The blend of claim 11, wherein the long chain fatty acid comprises a mixture of 73 to 95% linear fatty acids and 5 to 27% branched fatty acids based on the total weight of long chain fatty acids present.

14. The blend of claim 1, which contains at most 2% by weight of water.

* * * * *